United States Patent
Woolverton et al.

(10) Patent No.: US 7,407,815 B2
(45) Date of Patent: Aug. 5, 2008

(54) LIQUID CRYSTAL CASSETTE

(75) Inventors: Christopher J. Woolverton, Kent, OH (US); Gary D. Niehaus, Kent, OH (US)

(73) Assignees: Kent State University, Kent, OH (US); Northeastern Ohio Universities College of Medicine, Rootstown, OH (US)

( * ) Notice: Subject to any disclaimer, the term of this patent is extended or adjusted under 35 U.S.C. 154(b) by 0 days.

(21) Appl. No.: 11/535,739

(22) Filed: Sep. 27, 2006

(65) Prior Publication Data

US 2007/0092868 A1  Apr. 26, 2007

Related U.S. Application Data

(60) Provisional application No. 60/596,486, filed on Sep. 28, 2005.

(51) Int. Cl.
*G01N 33/543* (2006.01)

(52) U.S. Cl. ............ 436/518; 422/56; 422/58; 435/287.1; 435/287.2; 435/288.4; 435/288.5; 435/810; 436/164; 436/524; 436/527; 436/805

(58) Field of Classification Search .............. None
See application file for complete search history.

(56) References Cited

U.S. PATENT DOCUMENTS

| 4,467,032 | A | 8/1984 | Lowke et al. |
| 6,171,802 | B1 | 1/2001 | Woolverton et al. |
| 6,797,463 | B2 | 9/2004 | Abbott et al. |
| 2004/0185551 | A1* | 9/2004 | Niehaus ............ 435/287.2 |

* cited by examiner

*Primary Examiner*—Christopher L Chin
(74) *Attorney, Agent, or Firm*—Hahn Loeser & Parks, LLP

(57) ABSTRACT

A functional cassette for the detection of ligands comprises a first inner housing, a second middle housing and a third outer housing and each housing is at least partially rotatable relative to an adjoining housing. The first inner housing contains a central well adapted for receiving a sample, and the central well is in selectable fluid communication with at least one mixing chambers. The mixing chambers contain a reagent for forming a complex with a ligand. The first inner housing additionally comprises at least one compartments for the storage of a liquid crystalline material, and the compartments are in selectable fluid communication with at least one mixing chambers. The third outer housing comprises at least one detection chambers for observing the light transmission properties of a liquid crystal material and the detection chambers are in selectable fluid communication with the mixing.

20 Claims, 6 Drawing Sheets

LIQUID CRYSTAL CASSETTE

CROSS-REFERENCE TO RELATED APPLICATIONS/INCORPORATION BY REFERENCE

The present application claims priority from U.S. provisional application Ser. No. 60/596,486, filed Sep. 28, 2005. The disclosure of application Ser. No. 60/596,486 is hereby incorporated by reference.

TECHNICAL FIELD

This invention relates to the detection of a ligand by a receptor. More particularly, this invention relates to a cassette that houses specific antibodies and a liquid crystalline material to detect antigens. Even more particularly, this invention relates to a cassette to house and utilize components for detection of ligands.

BACKGROUND OF THE INVENTION

The detection of a ligand by a receptor (for example, detection of a pathogenic agent such as a microbe or toxin by an antibody; or detection of an antibody in blood by another antibody; or binding of a chemical toxin, such as nerve gas, to its receptor) is important in the diagnosis and treatment of individuals exposed to disease-causing or toxic agents. Early detection of pathogenic agents can be a great benefit in either disease prophylaxis or therapy before symptoms appear or worsen.

Every species, strain or toxin of a microbe contains unique surface ligands. Using molecular engineering and/or immunological techniques, receptor molecules, such as antibodies, can be isolated that will bind to these ligands with high specificity. Methods have also been developed where receptors, such as antibodies, are linked to a signaling mechanism that is activated upon binding.

Many available diagnostic tests are antibody based, and can be used to detect either a disease-causing agent or a biologic product produced by the patient in response to the agent. There are currently three prevailing methods of antibody production for recognition of ligands (antigens): polyclonal antibody production in whole animals with recognition for multiple epitopes, monoclonal antibody production in transformed cell lines with recognition for a single epitope (after screening), and molecularly engineered phage displayed antibody production in bacteria with recognition of a single epitope (after screening). Each of these receptor systems is capable of binding and identifying a ligand, but the sensitivity of each is limited by the particular immunoassay detection system to which it is interfaced.

Immunoassays, such as enzyme-linked immunosorbent assay (ELISA), enzyme immunoassay (EIA), and radioimmunoassay (RIA), are well known for the detection of antigens. The basic principle in many of these assays is that an enzyme-, chromogen-, fluorogen-, or radionucleotide-conjugated antibody permits antigen detection upon antibody binding. In order for this interaction to be detected as a color, fluorescence or radioactivity change, significant numbers of antibodies must be bound to a correspondingly large number of antigen epitopes.

A system for detecting ligands which utilizes an amplification mechanism such as an antibody embedded liquid crystalline material is provided by U.S. Pat. No. 6,171,802, the disclosure of which is incorporated herein by reference. There is a need, however, for a cassette for rapid, reliable, and automatic detection of ligands, especially when present in very small quantities, that provides a measurable signal.

SUMMARY OF THE INVENTION

It is, therefore, an aspect of the present invention to provide a functional cassette or cassette, for the detection of ligands with high sensitivity and specificity.

It is another aspect of the present invention to provide a cassette for the storage of a liquid crystalline material and an antibody against an antigen to be detected, receipt of a sample, mixing of the sample with the antibody, and the detection of any resulting immune complexes.

In general, the present invention provides a functional cassette for the detection of ligands including a first inner housing, a second middle housing and a third outer housing, wherein each housing is at least partially rotatable relative to an adjoining housing, wherein the first inner housing contains a central well adapted for receiving a sample, and the central well is in fluid communication with at least one mixing chamber located within the second middle housing when the first inner housing is in a first position relative to the second middle housing, wherein the at least one mixing chamber contains at least one receptor capable of binding to a specific type of ligand to form a receptor-ligand complex, wherein the first inner housing further comprises at least one compartment adapted for the storage of a liquid crystalline material, wherein the at least one compartment is in fluid communication with at least one mixing chamber when the first inner housing is in a second position relative to the second middle housing, wherein the third outer housing comprises at least one detection chamber for observing a signal generated after formation of the receptor-ligand complex, and wherein the at least one detection chamber is in fluid communication with the at least one mixing chamber when the third outer housing is in a first position relative to the second middle housing.

In a further embodiment of the present invention, a method of detecting a ligand includes providing a cassette, the cassette includes a first inner housing, a second middle housing and a third outer housing, wherein each housing is at least partially rotatable relative to an adjoining housing, wherein the first inner housing contains a central well adapted for receiving a sample, and the central well is in fluid communication with at least one mixing chambers when the first inner housing is in a first position relative to the second middle housing, wherein the at least one mixing chamber contains at least one receptor capable of binding to a ligand to form a receptor-ligand complex, and wherein the first inner housing further comprises at least one liquid crystalline storage compartment for the storage of a liquid crystalline material, wherein the at least one compartment is in fluid communication with at least one mixing chamber located within the second middle housing when the first inner housing is in a second position relative to the second middle housing. The method also includes depositing a sample to be tested into the central well, performing a first centrifugation on the cassette with the first inner housing in a first position relative to the second middle housing, rotating the first inner housing to a second position relative to the second middle housing, performing a second centrifugation on the cassette, rotating the third outer housing to a second position relative to the second middle housing, performing a third centrifugation on the cassette, and examining the light transmission properties of the liquid crystal material in the detection chambers.

Another embodiment of the present invention includes detecting a plurality of ligands by providing a cassette that includes a first inner housing, a second middle housing and a third outer housing, wherein each housing is at least partially rotatable relative to an adjoining housing, wherein the first inner housing contains a central well adapted for receiving a sample, and the central well is in fluid communication with at least one mixing chambers when the first inner housing is in a first position relative to the second middle housing, wherein the at least one mixing chamber contains includes a plurality of receptors raised against a plurality of ligands, wherein each receptor is capable of binding to a specific receptor to form a plurality of receptor-ligand complexes, wherein the first inner housing further comprises at least one liquid crystalline storage compartment for the storage of a liquid crystalline material, wherein the at least one compartment is in fluid communication with at least one mixing chamber located within the second middle housing when the first inner housing is in a second position relative to the second middle housing. The method also includes depositing a sample to be tested into the central well, performing a first centrifugation on the cassette with the first inner housing in a first position relative to the second middle housing, rotating the first inner housing to a second position relative to the second middle housing, performing a second centrifugation on the cassette, rotating the third outer housing to a second position relative to the second middle housing, performing a third centrifugation on the cassette, and examining the light transmission properties of the liquid crystal material in the detection chambers.

DETAILED DESCRIPTION OF THE INVENTION

Figure 1:
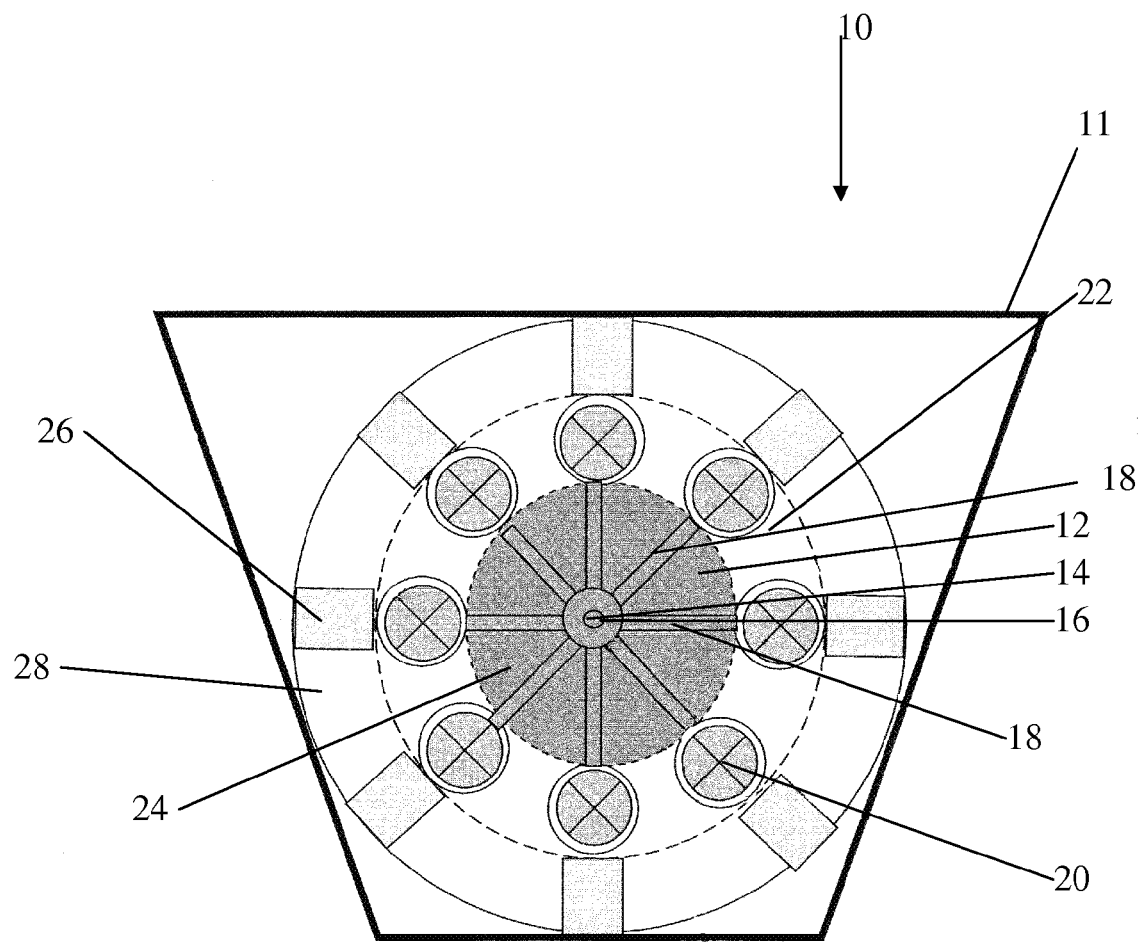
FIG. 1 is a top plan view of the cassette of the present invention.
Figure 2:
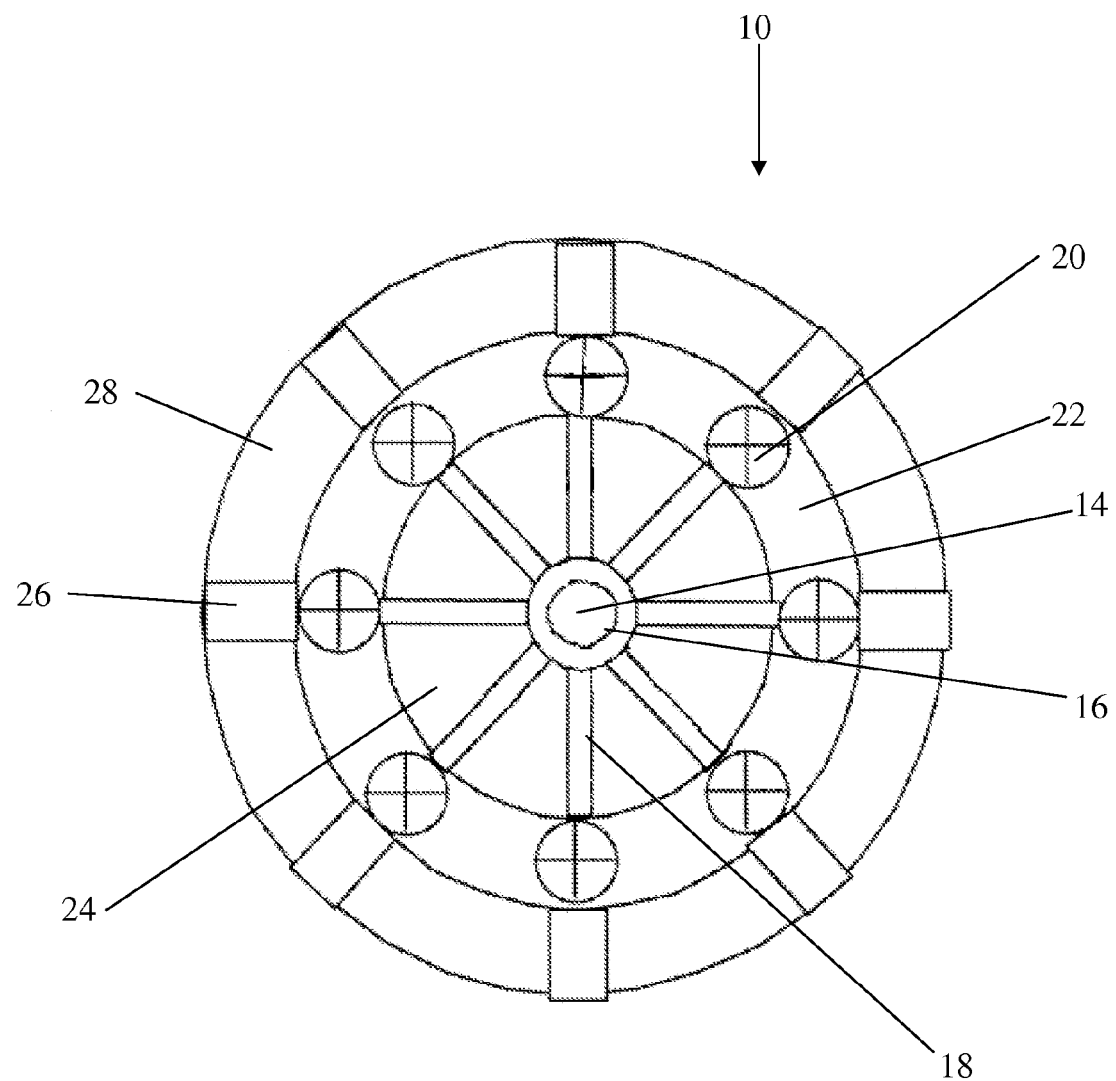
FIG. 2 is a top plan view of the housings of the cassette of the present invention.
Figure 3:
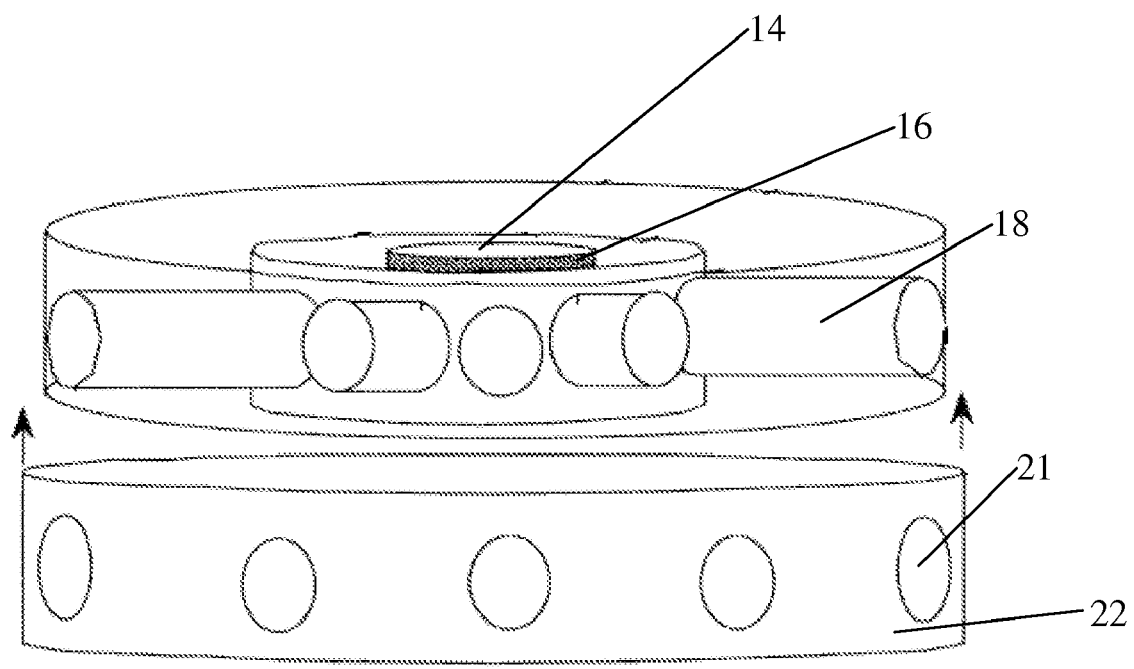
FIG. 3 is a side perspective view of the first inner housing and the inner wall of the second middle housing.
Figure 4:
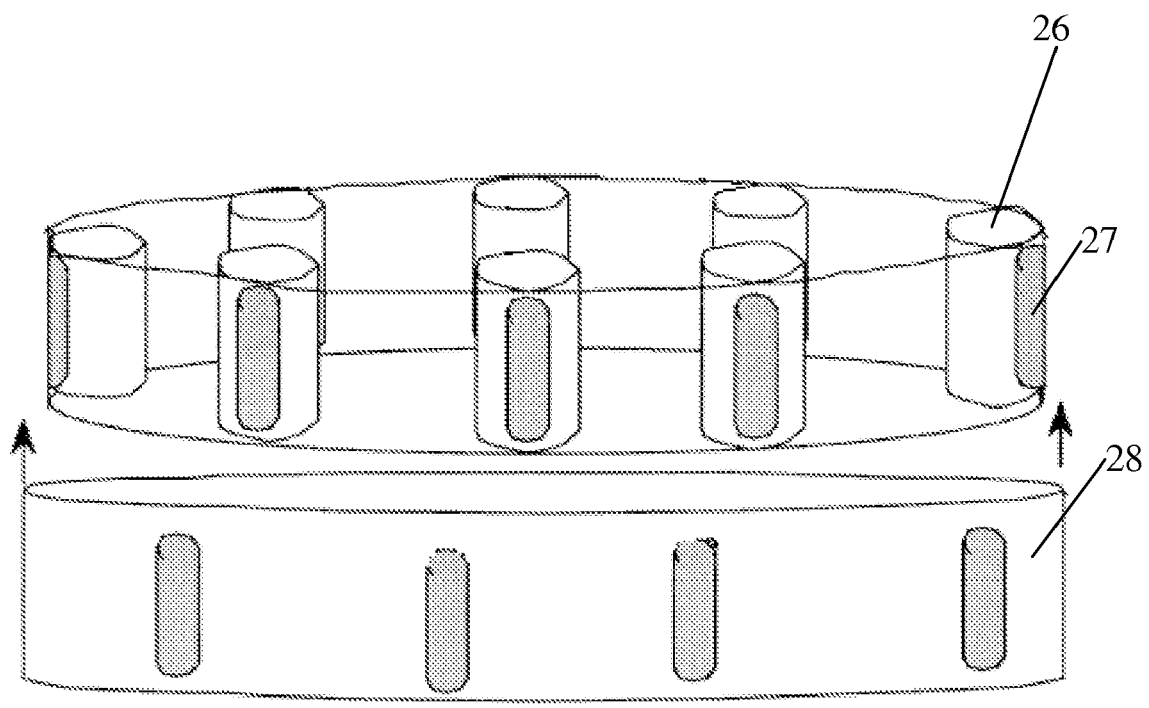
FIG. 4 is a side perspective view of the second middle housing and the inner wall of the third outer housing.
Figure 5:
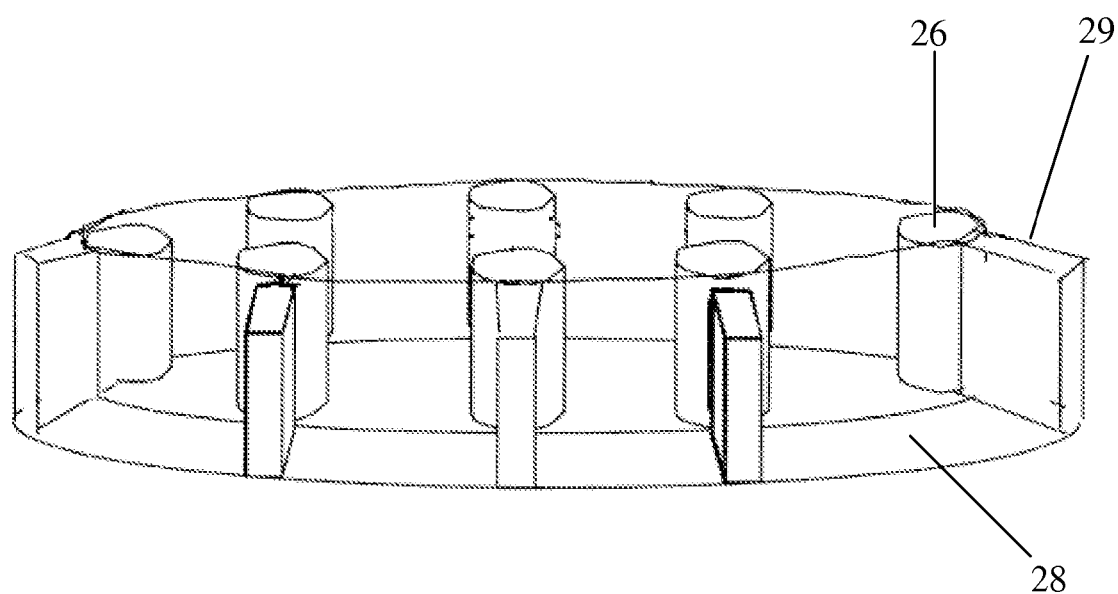
FIG. 5 is a side perspective view of the mixing chambers of the second middle housing and the detection chambers of the third outer housing.

The present invention is directed toward a cassette or biochip for the detection of ligands such as pathogenic agents including bacteria, pathogenic viruses and toxins. The cassette contains compartments to store test reagents or receptors, receive a specimen or ligand to be tested, mix the receptors with the ligand, and provide a detectable positive signal when a binding reaction occurs between the receptor and the ligand. The receptor of the test will typically include an antibody raised against a particular antigen to be detected, and a liquid crystalline material. When an antibody recognizes a particular ligand, a reaction occurs between the antigen and the antibody to form an immune complex. This immune complex will alter the light transmission properties of the liquid crystalline material compared to a liquid crystalline material without the presence of immune complexes.

Any receptor, such as antibodies or biologic/biologically engineered receptors for ligands, can be incorporated into the device as long as binding of the ligand to the receptor causes a detectable distortion of the receptor. For example, any type of monospecific antibody (polyclonal, monoclonal, or phage displayed) can effectively function as a receptor, and thus each of those antibody types will be described in the following paragraphs. Although phage-displayed antibodies can be expeditiously modified for identification of new ligands and are used as receptor examples in this patent application, any physically-distortable receptor-ligand interaction is appropriate for the detection component.

Other receptors include polyclonal and monoclonal antibodies. Injection of a purified ligand (antigen) into a host animal stimulates the immune system to produce an array of antibodies against various reactive sites on the antigen. Since several lymphocytes are responding to different antigenic epitopes, a multi-specific antibody cocktail (polyclonal) is created and can be purified for antigen detection. Antibody-producing spleen cells (B lymphocytes) are fused with immortalized myeloma cells to create hybridomas which provide nearly infinite quantities of antibody with a single, defined specificity. Interstrain and even interspecies hybrids of these 'monoclonal'antibodies can be generated through genetic engineering techniques. These highly specific antibodies have significant therapeutic potential, as evidenced by the U.S. Food and Drug Administration's approval of the use of mouse-human chimeric antibodies for treatment of selected diseases.

Any mechanism that permits detection of ligand-receptor complex formation functions as an amplifier and can be incorporated into the cassette of the present invention. In particular, a liquid crystal will amplify the distortion caused when a ligand binds to a receptor. A liquid crystal is a state of matter in which molecules exhibit some orientational order but little positional order. This intermediate ordering places liquid crystals between solids (which possess both positional and orientational order) and isotropic fluids (which exhibit no long-range order). Solid crystal or isotropic fluid can be caused to transition into a liquid crystal by changing temperature (creating a thermotropic liquid crystal) or by using an appropriate diluting solvent to change the concentration of solid crystal (creating a lyotropic liquid crystal). Lyotropic liquid crystals will be used for our amplification system.

An example of the cassette of the present invention may be described with reference to the FIGS. 1-5. As shown in the FIG. 1, the cassette 10 may have an outer portion 11 with a shape, such as a trapezoid, that requires a predetermined orientation of the cassette in a detector or other laboratory detection apparatus. Located within the cassette 10 is a plurality of compartments arranged in a plurality of concentric rings or housings. The first and innermost housing 12 has a centrally located sample well or chamber 14. Optionally surrounding the sample well 14 in the first housing 12 is a cell filter 16 that permits separation of a liquid fraction of a specimen from whole cells or other solid material when placed within the sample well 14. The filtered sample chamber 14 communicates with at least one sample channel 18 that connect the filtered sample chamber 14 to at least one concentrically surrounding mixing chambers 20 in a second middle housing 22. Adjoining but separated from the sample channels 18 in the first housing 12 is at least one liquid crystal reservoir 24. Concentrically surrounding the mixing chambers is at least one corresponding detection chamber 26 in a third or outer housing 28. The top and bottom of the at least one detection chamber 26 may be constructed of a transparent material such as a polymer coated, optical glass.

In use, a specimen to be tested is placed in the center sample well or chamber 14 located within inner housing 12. The cassette 10 is centrifuged to drive the liquid portion of a specimen across the cell filter 16 and into filtered sample chamber 14. The filtered specimen then travels through the sample channels 18 and into the mixing chambers 20. In the mixing chambers 20, the sample (containing ligands to be detected) is mixed with a receptor, in one case an antibody or other identification reagent may be used, that was previously stored in the mixing chamber 20, essentially creating ligand-receptor complexes. The receptor may be an antibody that has been lyophilized to permit for long-term storage of the cassette 10 prior to use. When a lyophilized antibody is used, liquid from the specimen is permitted to re-hydrate the antibody in mixing chamber 20. A magnetic stir bar or other stirring aid may be present in the mixing chamber 20 to accelerate re-hydration of the antibody. The mixing chambers 20 may have double vented walls to prevent passage of the liquid contained therein into an adjoining chamber until desired. After a predetermined period of time to allow for re-hydration of the antibody and reaction of the antibody to an antigen present in the liquid portion of the specimen, the second middle housing 22 is rotated relative to the first inner housing 12 to permit communication through at least one aperture 21 in second middle housing between the mixing chamber 20 and the liquid crystal reservoirs 24. A second centrifugation moves the liquid crystal material from the liquid crystal reservoir to the mixing chamber 20, thereby mixing the antibody, specimen and liquid crystal material, thus in effect, creating ligand-receptor complexes within the liquid crystal bulk. The third outer housing 28 is then rotated relative to the second middle housing 22 to permit communication between the mixing chamber 20 and the detection chamber 26 wherein a viewable portion 27 of the detection chamber 26 is aligned with a viewable portion 29 of the outer third housing 28. A third centrifugation moves the ligand-receptor complexes within the liquid crystalline medium into the detection chamber 26. The cassette 10 is then placed in a detection device and the transmission of light through the ligand-receptor complex (for example an antibody-specimen complex) and liquid crystal mixture is measured. When the ligand-receptor complex forms, it alters the light transmission properties of the liquid crystal material. When a ligand is not present in the specimen however, no ligand-receptor complex forms and therefore, the transmission properties of the liquid crystal material are unchanged when compared to that of the liquid crystal material alone.

Figure 6:
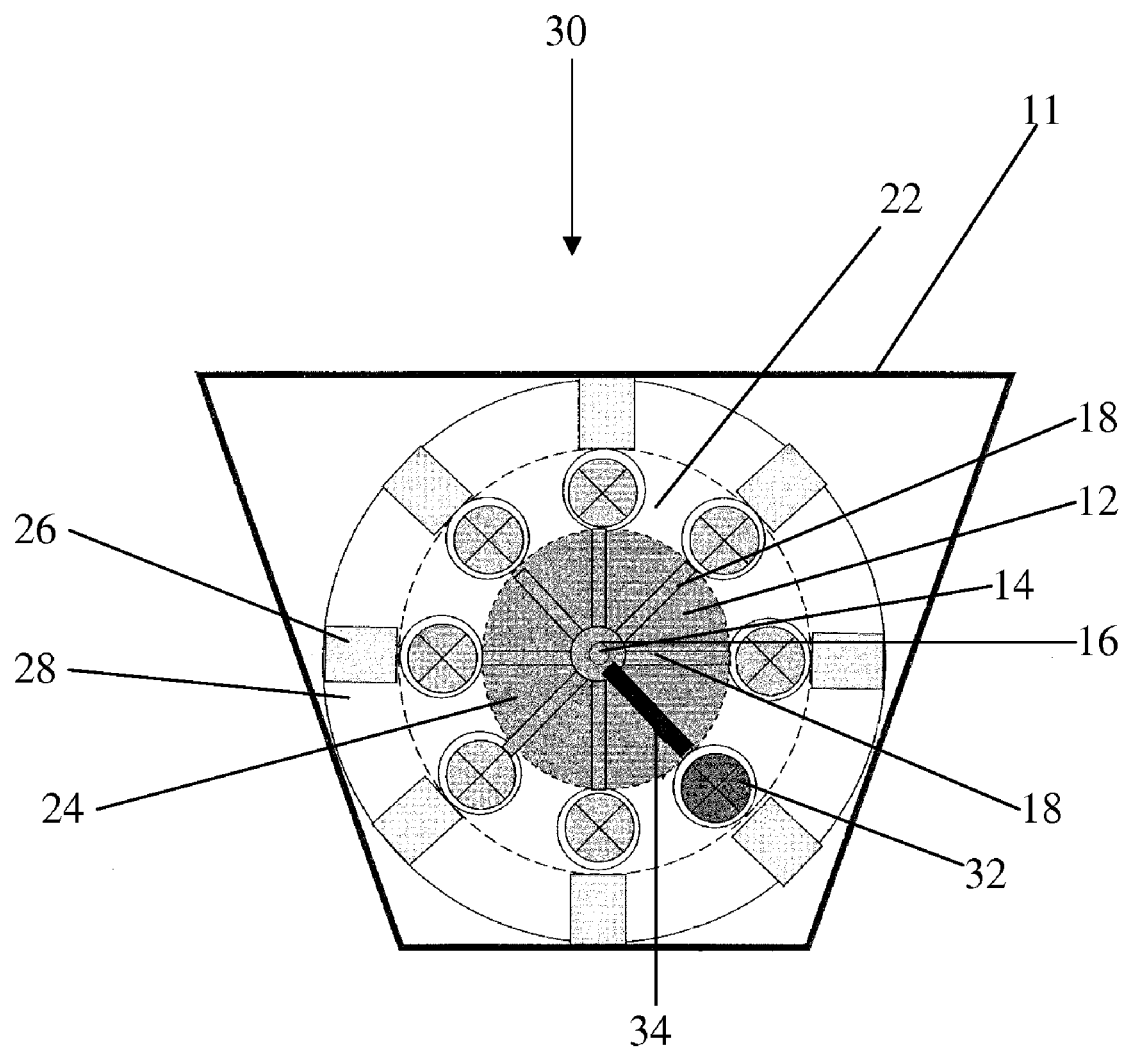
FIG. 6 is a top plan view of another embodiment of a cassette of the present invention.

In a further embodiment of the present invention, as seen in FIG. 6, the cassette 30 may include a control mixing chamber 32 for a non-clinical antibody control, where the corresponding sample channel 34 is occluded to prevent transfer of the sample into the control mixing chamber 32. The cassette 10 may also contain more than one mixing chamber with an antibody raised against different antigens in each mixing chamber so that a single cassette may be used to detect a plurality of ligands.

Based upon the foregoing disclosure, it should now be apparent that cassette of the present invention will carry out the objects set forth hereinabove. It is, therefore, to be understood that any variations evident fall within the scope of the claimed invention and thus, the selection of specific component elements can be determined without departing from the spirit of the invention herein disclosed and described.

We claim:

1. A functional cassette for the detection of ligands comprising:
    a first housing, a second housing and a third housing;
    wherein each housing is at least partially rotatable relative to an adjoining housing;
    wherein the first housing contains a sample well to receive a sample, and the sample well is in fluid communication with at least one mixing chamber located within the second housing when the first housing is in a first position relative to the second housing;
    wherein the at least one mixing chamber contains at least one receptor bindable to a specific type of ligand to form a receptor-ligand complex;
    at least one compartment for storing a liquid crystalline material, wherein the at least one compartment is in fluid communication with the at least one mixing chamber when the first housing is in a second position relative to the second housing;
    wherein the third housing comprises at least one detection chamber for observing a signal generated after formation of the receptor-ligand complex; and
    wherein the at least one detection chamber is in fluid communication with the at least one mixing chamber when the third housing is in a first position relative to the second housing.

2. The cassette of claim 1, wherein the ligand is a pathogenic agent or product of a pathogenic agent.

3. The cassette of claim 2, wherein the at least one receptor is an antibody.

4. The cassette of claim 3, wherein the ligand is bindable to a specific antibody.

5. The cassette of claim 1, wherein liquid crystalline material is selected from the group consisting of thermotropic and lyotropic liquid crystalline materials.

6. The cassette of claim 1, wherein the signal is generated by a change in light transmission properties of the liquid crystalline material.

7. The cassette of claim 1, wherein the signal is optically observable.

8. The cassette of claim 1 further comprising a control mixing chamber.

9. The cassette of claim 8, wherein the control mixing chamber is manipulated to prevent the transfer of the sample into the at least one control mixing chamber.

10. The cassette of claim 1, wherein the at least one mixing chamber includes a plurality of receptors bindable to a plurality of ligands, wherein the cassette detects a plurality of ligands.

11. The cassette of claim 1 further comprising at least one sample channel that connects the sample well with at least one mixing chambers.

12. A method of detecting a ligand, the method comprising:
    providing a cassette, the cassette comprising:
        a first housing, a second housing and a third housing;
        wherein each housing is at least partially rotatable relative to an adjoining housing;
        wherein the first housing contains a sample well to receive a sample, and the sample well is in fluid communication with at least one mixing chamber located in the second housing when the first housing is in a first position relative to the second housing;
        wherein the at least one mixing chamber contains at least one receptor bindable to a ligand to form a receptor-ligand complex;
        at least one liquid crystalline storage compartment for the storage of a liquid crystalline material,
    depositing a sample to be tested into the sample well;
    performing a first centrifugation on the cassette with the first housing in a first position relative to the second housing to introduce at least a portion of the sample from the sample well to the mixing chamber;
    rotating the first housing to a second position relative to the second housing to permit fluid communication through at least one aperture of the second housing between the mixing chamber and at least one storage compartment of the liquid crystalline material;

performing a second centrifugation on the cassette to introduce at least a portion of the liquid crystalline material from the storage compartment to the mixing chamber;

rotating the third housing to a second position relative to the second housing;

performing a third centrifugation on the cassette to introduce at least a portion of the contents of the mixing chamber to the detection chamber;

placing the cassette into a detection device, wherein the detection device transmits light toward the liquid crystal material; and examining the light transmission properties of the liquid crystal material in the detection chambers, wherein the light transmission properties are indicative of the detection of a ligand.

13. The method of claim 12, wherein a portion of the sample moves from the sample well through at least one channel into the mixing chamber during the first centrifugation to promote the formation of the receptor-ligand complex.

14. The method of claim 12, wherein the liquid crystalline material moves from the liquid crystalline storage compartment into the mixing chamber during the second centrifugation to promote mixing with the at least one receptor.

15. The method of claim 12, wherein the ligand is a pathogenic agent or product of a pathogenic agent.

16. The method of claim 12, wherein the at least one receptor is an antibody.

17. The method of claim 12, wherein at least one liquid crystalline material is selected from the group consisting of thermotropic and lyotropic liquid crystalline materials.

18. The method of claim 12, wherein a signal is generated by a change in light transmission properties of the liquid crystalline material.

19. The method of claim 18, wherein the signal is optically observable.

20. A method of detecting a plurality of ligands, the method comprising:

providing a cassette, the cassette comprising:
a first housing,
a second housing having a plurality of mixing chambers, with each mixing chamber including at least one receptor bindable to a specific type of ligand, wherein a different type of receptor is provided in different ones of the mixing chambers;
a third housing having a plurality of detection chambers, each detection chamber correlating to one of the plurality of mixing chambers, wherein each housing is at least partially rotatable relative to an adjoining housing;
wherein the first housing contains a sample well to receive a sample, and the sample well is in fluid communication with at least one mixing chamber located within the second housing when the first housing is in a first position relative to the second housing;
at least one liquid crystalline storage compartment for the storage of a liquid crystalline material, depositing a sample to be tested into the sample well;

performing a first centrifugation on the cassette with the first housing in a first position relative to the second housing to introduce a portion of the sample from the sample well to the mixing chamber;

rotating the first housing to a second position relative to the second housing to permit fluid communication through at least one aperture of the second housing between the mixing chamber and at least one storage compartment of the liquid crystalline material;

performing a second centrifugation on the cassette to introduce the liquid crystalline material into the mixing chamber;

rotating the third housing to a second position relative to the second housing;

performing a third centrifugation on the cassette to move at least some material from the mixing chamber to the detection chamber;

placing the cassette into a detection device, wherein the detection device transmits light toward the liquid crystal material; and examining the light transmission properties of the liquid crystal material in the detection chambers, wherein the light transmission properties are indicative of the detection of a ligand.

* * * * *